US011564955B2

(12) United States Patent
Lee et al.

(10) Patent No.: US 11,564,955 B2
(45) Date of Patent: Jan. 31, 2023

(54) COMPOSITION INCLUDING, AS ACTIVE INGREDIENT, STRAIN HAVING ABILITY TO PRODUCE FORMIC ACID FOR PREVENTING OR TREATING OBESITY OR METABOLIC SYNDROMES CAUSED BY OBESITY

(71) Applicant: KOREA FOOD RESEARCH INSTITUTE, Wanju-gun Jeollabuk-do (KR)

(72) Inventors: Myung Ki Lee, Gyeonggi-do (KR); Sang Dong Lim, Gyeonggi-do (KR); Sung Hun Yi, Daejeon (KR); Yong Sun Cho, Seoul (KR); Young Do Nam, Gyeonggi-do (KR); Jin Ju Bae, Daejeon (KR)

(73) Assignee: KOREA FOOD RESEARCH INSTITUTE, Wanju-Gun Jeollabuk-Do (KR)

( * ) Notice: Subject to any disclaimer, the term of this patent is extended or adjusted under 35 U.S.C. 154(b) by 215 days.

(21) Appl. No.: 16/462,901

(22) PCT Filed: Nov. 21, 2017

(86) PCT No.: PCT/KR2017/013297
§ 371 (c)(1),
(2) Date: Dec. 2, 2020

(87) PCT Pub. No.: WO2018/093238
PCT Pub. Date: May 24, 2018

(65) Prior Publication Data
US 2021/0315946 A1 Oct. 14, 2021

(30) Foreign Application Priority Data
Nov. 21, 2016 (KR) .................. 10-2016-0154978

(51) Int. Cl.
*A61K 35/744* (2015.01)
*A23L 33/135* (2016.01)

(52) U.S. Cl.
CPC .......... *A61K 35/744* (2013.01); *A23L 33/135* (2016.08)

(58) Field of Classification Search
None
See application file for complete search history.

(56) References Cited

U.S. PATENT DOCUMENTS 8,597,929 B2 * 12/2013 Kringelum ............... C12N 1/04
536/28.4
9,387,228 B2 * 7/2016 Sugiyama ............... A61K 35/74

FOREIGN PATENT DOCUMENTS

| EP | 2716167 A1 | 4/2014 |
|---|---|---|
| JP | S63280027 A | 11/1988 |
| JP | 2002-080357 A | 3/2002 |
| JP | 2002-530326 A | 9/2002 |
| KR | 10-2013-0001744 A | 1/2013 |
| KR | 10-1508586 B1 | 3/2015 |
| KR | 101508586 * | 4/2015 |
| KR | 10-1611829 B1 | 4/2016 |
| KR | 101611829 * | 4/2016 |
| KR | 10-2016-0066253 A | 6/2016 |
| WO | 2010098131 A1 | 8/2005 |
| WO | 2005077390 A1 | 8/2007 |
| WO | 2018045492 A1 | 3/2018 |
| WO | 2018045493 A1 | 3/2018 |

OTHER PUBLICATIONS

Japanese Patent Office, Decision to Grant a Patent, JP Application No. 2019-547566, dated Dec. 17, 2021 in 6 pages.
Japanese Patent Office, Notice of Reasons for Refusal, JP Application No. 2019-547566, dated Sep. 14, 2020 in 13 pages.
Japanese Patent Office, Notice of Reasons for Refusal, JP Application No. 2019-547566, dated Mar. 23, 2021 in 6 pages.
Japanese Patent Office, Notice of Reasons for Refusal, JP Application No. 2019-547566, dated Aug. 25, 2021 in 6 pages.
Akhtar et al., Anti-Diabetic Activity and Metabolic Changes Induced by Andrographis Paniculata Plant Extract in Obese Diabetic Rats, dated Aug. 9, 2016, in 19 pages.
Aoki, Tsugutoshi, Inborn Errors of Metabolism, dated May 26, 1998, in 10 pages.
KIPO Notification of Reason for Refusal for KR 10-2016-0154978, dated Feb. 1, 2018, in 11 pages.
Hlivak et al., "One-year application of probiotic strain Enterococcus faecium M-74 decreases serum cholesterol levels," Bratisl Lek Listy 2005; 106 (2): 67-72.
Shimabukuro, M. et al. "Lipoapoptosis in Beta-cells of Obese Prediabetic fa/fa Rats" The Journal of Biological Chemistry, Dec. 4, 1998, pp. 32487-32490; vol. 273, No. 49; (5 pages).
Lowell, BB. et al. "Towards a molecular understanding of adaptive thermogenesis" Nature, Apr. 6, 2000; pp. 652-660; vol. 404 (11 pages).

(Continued)

Primary Examiner — Vera Afremova
(74) Attorney, Agent, or Firm — Procopio, Cory, Hargreaves & Savitch LLP

(57) ABSTRACT

The present invention relates to a composition comprising as an active ingredient a strain having excellent ability to produce formic acid for preventing or treating obesity or metabolic syndromes caused by obesity; and to a food composition and a health functional food each comprising the active ingredient. The strain having excellent ability to produce formic acid according to the present invention not only has effects of reducing body weight and inhibiting fat accumulation in organs, but also has activity to effectively lower blood triglyceride and cholesterol levels, and therefore, the composition comprising the strain as an active ingredient can be favorably used as a composition capable of preventing/alleviating or treating obesity or metabolic syndromes caused by obesity. Therefore, the strain having excellent ability to produce formic acid according to the present invention can be favorably used as a material for a medical product or health food.

3 Claims, 2 Drawing Sheets

(56) References Cited

OTHER PUBLICATIONS

Ahn, IS et al., "Weight control mechanisms and antiobesity functional agents" Journal of the Korean Society of Food Science and Nutrition, Apr. 30, 2007, pp. 503-513; vol. 36, No. 4; English abstract provided. (11 pages).
Hirsch, J. et al. "Methods for the determination of adipose cell size in man and animals" Journal of Lipid Research, 1968; pp. 110-119; vol. 9 (10 pages).
Park, SH. et al. "Euonymus alatus prevents the hyperglycemia and hyperlipidemia induced by high-fat diet in ICR mice" Journal of Ethnopharmacology, Dec. 1, 2005; pp. 326-335; vol. 102, Issue 3 (10 pages).
International Search Report and Written Opinion of International Application No. PCT/KR2017/013297, dated Feb. 19, 2018; English translation of ISR provided; 9 pages.

\* cited by examiner

| | | | |
|---|---|---|---|
| A |  | B |  |
| A size | 2026.75±257.16μm² | B size | 4600.18±558.57μm² |
| C |  | D |  |
| C size | 3546.49±264.77μm² | D size | 3490.73±527.97μm² |
| E |  | | |
| E size | 4265.01±238.07μm² | | |

COMPOSITION INCLUDING, AS ACTIVE INGREDIENT, STRAIN HAVING ABILITY TO PRODUCE FORMIC ACID FOR PREVENTING OR TREATING OBESITY OR METABOLIC SYNDROMES CAUSED BY OBESITY

CROSS-REFERENCE TO RELATED APPLICATIONS

This application is a U.S. National Stage entry of PCT Application No: PCT/KR2017/013297 filed Nov. 21, 2017, which claims priority to Korean Patent Application No. 10-2016-0154978, filed Nov. 21, 2016, the contents of which are incorporated herein by reference.

TECHNICAL FIELD

The present disclosure relates to a composition containing, as an active ingredient, a strain having excellent formic acid producing ability for preventing or treating obesity or metabolic syndrome caused by obesity, and to a food composition and a health functional food each containing the active ingredient.

BACKGROUND ART

Recently, the improvement of living standards due to economic development has enhanced the hygiene environment, but frequent intakes of instant foods and changes of dietary life into meat-based consumption cause intake of excessive calories. However, such changes in the dietary life of modern people has resulted in a fast increase tendency of obese population since the amount of calories consumed is small due to vastly insufficient amount of exercise. Obesity not only causes external problems, but has also been reported to cause several diseases, that is, breast cancer, uterine cancer, and colorectal cancer as well as adult diseases, such as hypertension, diabetes, hyperlipidemia, and coronary artery disease, due to the persistence of obesity, and thus obesity is now treated as one of the deadly diseases [J. Biol. Chem., 273, 32487-32490 (1998); and Nature, 404, 652-660 (2000)].

Obesity has increased by 75% globally since 1980, and in the United States, 33% and 26% of the population is reported to be overweight and obese, respectively (Ahn I S, Park K Y, Do M S. 2007. Weight control mechanisms and antiobesity functional agents. J Korean Soc Food Sci Nutr 36: 503-513). In Korea, the obesity population is also steadily increasing, and according to the 2007 National Health and Nutrition Examination Survey, the obese population has rapidly increased from 26.3% in 1998 to 31.7% in 2005.

This obesity is caused by an imbalance of energy intake and consumption, and excess energy is converted into fat cells and stored in the body. Free fatty acids, cytokines, and the like, which are secreted from accumulated fat cells, cause insulin resistance and increase the inflammatory response, leading to direct causes of chronic disease, such as metabolic syndrome, diabetes, cardiovascular disease, and cancer. In order to treat such obesity, the improvement of eating habits and lifestyle through exercise and diet therapy and the treatment through drug therapy and surgery are introduced, and out of these, as for the development of anti-obesity drugs to suppress obesity, more than 100 kinds of medicines are being sold or under development in the United States, and the market scale therefor is expected to gradually grow in size.

Current medicines for treating obesity may be largely classified into drugs that act on the central nervous system to affect appetite and drugs that act on the gastrointestinal tract to inhibit absorption. The drugs acting on the central nervous system include, depending on the mechanism of each drug, those inhibiting serotonin (5-HT) in the nervous system, such as fenfluramine and dexfenfluramine, those acting on noradrenaline in the nervous system, such as ephedrine and caffeine, and those acting on both serotonin and noradrenaline in the nervous systems to inhibit obesity, such as sibutramine, and these drugs are available in the market. Besides, a representative example of the drugs acting on the gastrointestinal tract to inhibit obesity is orlistat, which has recently been approved as an obesity drug since orlistat inhibits lipase produced in the pancreas to reduce the absorption of fat.

However, out of conventionally used drugs, fenfluramine or the like causes sides effects, such as primary pulmonary hypertension or cardiac valve lesion and thus the use thereof has been recently prohibited; sibutramine causes side effects of increasing blood pressure; and orlistat has been reported to have side effects, such as digestive disorders, fatty stools, fecal incontinence, and the inhibition of absorption of fat-soluble vitamins. Moreover, other chemically synthetic drugs cause problems, such as reduction in blood pressure or lactic acidosis, and thus could not be used for patients with cardiac insufficiency or kidney disease.

Therefore, there has been recently a growing interest in obesity medicines or anti-obesity health functional foods of natural substances having an action of inhibiting the accumulation of body fat, such as naturally-derived compounds, in order to discover an obesity treatment and prevention method causing fewer side effects and having better effects.

Meanwhile, metabolic syndrome refers to a syndrome that shows risk factors together, such as hypertriglyceridemia, hypertension, hyperglycemia, abnormal blood coagulation, and obesity. The symptoms per se are not fatal, but are likely to develop severe diseases, such as diabetes or ischemic cardiovascular diseases, resulting in a great threat to modern people.

The factors known in association with the causes and treatment of metabolic syndrome are exercise, dietary habits, weight, blood glucose, triglyceride, cholesterol, insulin resistance, adiponectin, leptin, AMPK activity, sex hormones such as estrogen, genetic factors, and the malonyl-CoA concentration in the body, and these are directly or indirectly involved therein.

It is known that the best ways to alleviate these symptoms of metabolic syndrome are exercise, diet restriction, and weight loss. The common denominator in such methods having an effect on metabolic syndrome is to promote energy metabolism to consume the excess energy in the body and thus prevent the accumulation of energy. Due to the lack of exercise relative to the intake of high calorie energy, such as through processed foods and fast foods, excess energy is accumulated as fat, causing various diseases including metabolic diseases. The effective removal of such excess energy is considered to be a method for treatment of metabolic diseases. It is considered to be essential to increase metabolic activity in order to effectively remove excess energy, and for this purpose, it is considered to be necessary to activate the factors involved in the inhibition of lipogenesis, the inhibition of glucogenesis, the stimulation of glucose consumption, the promotion of lipid oxidation, and the production promotion and activation of mitochondria, the core of energy metabolism.

Therefore, the present inventors, while seeking for a substance that causes no side effects on the living body and has excellent anti-obesity activity, analyzed various organic acids, which are differently contained in the feces between a normal group and an obesity group both of Koreans in their 50s, and as a result, the present inventors confirmed that the content of formic acid was remarkably higher compared with other organic acids in the normal group compared with the obesity group. In addition, the present inventors selected strains showing excellent formic acid producing ability among various strains producing organic acids, and confirmed that experimental groups, of which obesity animal models were orally administered with the finally selected three kinds of strains, showed effects of reducing body weight, inhibiting fat accumulation in organs, and effectively lowering blood triglyceride and cholesterol levels, and thus completed the present disclosure.

DETAILED DESCRIPTION OF THE INVENTION

Technical Problem

Therefore, an aspect of the present disclosure is to provide a composition for preventing or treating metabolic syndrome, the composition being capable of inhibiting body fat accumulation and effectively lowering blood fat and cholesterol levels.

Another aspect of the present disclosure is to provide a food composition for preventing or alleviating metabolic syndrome, the food composition being capable of inhibiting body fat accumulation and effectively lowering blood fat and cholesterol levels.

Still another aspect of the present disclosure is to provide a health functional food for preventing or alleviating metabolic syndrome, the health functional food being capable of inhibiting body fat accumulation and effectively lowering blood fat and cholesterol levels.

Technical Solution

In accordance with an aspect of the present disclosure, there is provided a pharmaceutical composition containing, as an active ingredient, a strain having formic acid producing ability, a culture thereof, a lysate thereof, or an extract thereof for preventing or treating metabolic syndrome.

The strain may be at least one species selected from the group consisting of *Enterococcus faecium* KR127 (accession number: KCTC 13135 BP), *Pediococcus pentosaceus* NKR654 (accession number: KCTC 13137 BP), and *Enterococcus faecalis* TN3 (accession number: KCTC 13136 BP).

The metabolic syndrome may be selected from the group consisting of obesity, diabetes, arteriosclerosis, hypertension, hyperlipidemia, liver diseases, stroke, myocardial infarction, ischemic diseases, and cardiovascular diseases.

The strain may be contained in a content of $10^7$-$10^{12}$ cfu/g relative to a total weight of the composition.

In accordance with another aspect of the present disclosure, there is provided a food composition containing, as an active ingredient, a strain having formic acid producing ability, a culture thereof, a lysate thereof, or an extract thereof for preventing or alleviating metabolic syndrome.

The strain may be at least one species selected from the group consisting of *Enterococcus faecium* KR127 (accession number: KCTC 13135 BP), *Pediococcus pentosaceus* NKR654 (accession number: KCTC 13137 BP), and *Enterococcus faecalis* TN3 (accession number: KCTC 13136 BP).

The metabolic syndrome may be selected from the group consisting of obesity, diabetes, arteriosclerosis, hypertension, hyperlipidemia, liver diseases, stroke, myocardial infarction, ischemic diseases, and cardiovascular diseases.

The strain may be contained in a content of $10^7$-$10^{12}$ cfu/g relative to a total weight of the composition.

The strain may reduce body weight and fat and lower blood cholesterol and triglyceride levels.

In accordance with still another aspect of the present disclosure, there is provided a health functional food containing, as an active ingredient, a strain having formic acid producing ability, a culture thereof, a lysate thereof, or an extract thereof for preventing or alleviating metabolic syndrome.

Advantageous Effects

The strain having excellent formic acid producing ability according to the present disclosure has not only effects of reducing body weight and inhibiting fat accumulation in organs, but also activity to effectively lower blood triglyceride and cholesterol levels, and thus the composition containing the same as an active ingredient can be helpfully used as a composition capable of preventing/alleviating or treating obesity or metabolic syndrome caused by obesity. Therefore, the strain having excellent formic acid producing ability according to the present disclosure can be helpfully used as a substance for medical products or health foods.

BEST MODE FOR CARRYING OUT THE INVENTION

Figure 1:
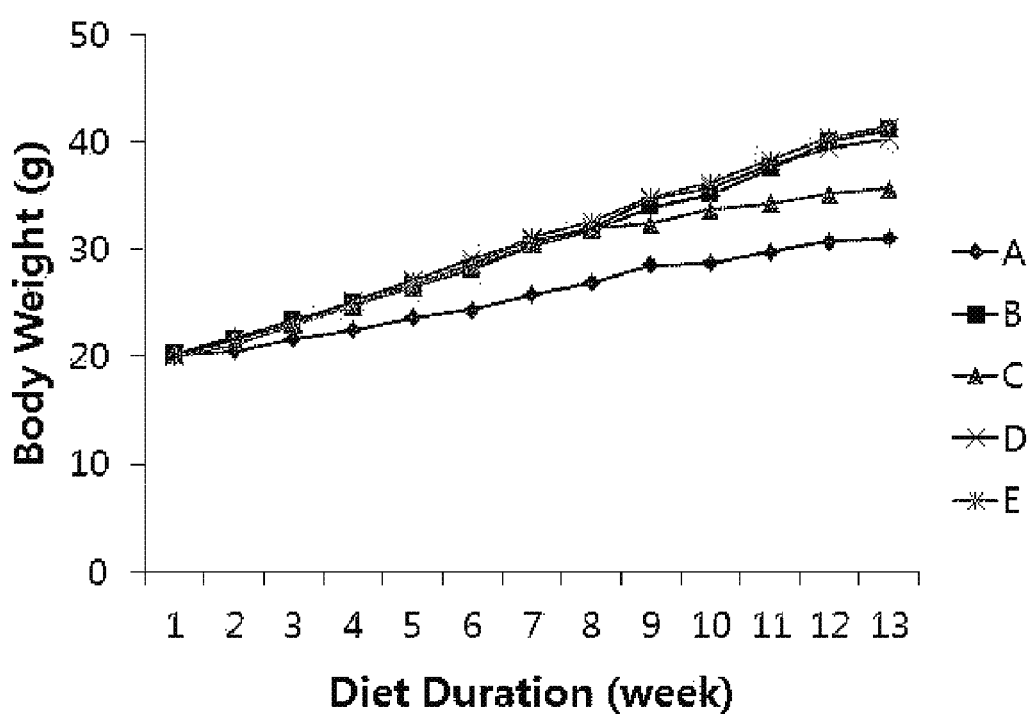
FIG. 1 is a graph illustrating changes in body weight over rearing time according to the feeding of various strains to high-fat diet-induced obesity experimental animals (A: normal diet group, B: high-fat diet group, C: high-fat diet+*Enterococcus faecium* KR127 feeding, D: high-fat diet+*Pediococcus pentosaceus* NKR654 feeding group, E: high-fat diet+*Enterococcus faecalis* TN3 feeding group).

Hereinafter, the terms used herein will be described.

As used herein, the term "culture" refers to a product obtained by culturing microorganisms in a known liquid medium or solid medium, and the term has a concept including microorganisms.

As used herein, the term "pharmaceutical acceptable" refers to not inhibiting biological activity and characteristics of an administered active substance without greatly stimulating an organism.

As used herein, the term "prevention" refers to all the activities that inhibit symptoms or delay the progression of a particular disease (e. g., obesity or metabolic syndrome) by the administration of the composition of the present disclosure.

As used herein, the term "treatment" refers to all the activities that alleviate or favorably modify symptoms of a particular disease (e. g., obesity or metabolic syndrome) by the administration of the composition of the present disclosure.

As used herein, the term "alleviation" refers to all the activities that at least reduce parameters associated with a condition to be treated, for example, the severity of symptoms.

As used herein, the term "administration" refers to providing an individual with a predetermined composition of the present disclosure through any appropriate method. The individual refers to any animal having a particular disease, of which symptoms can be alleviated by the administration of the composition of the present disclosure, such as a human being, a monkey, a dog, a goat, a pig, or a mouse.

As used herein, the term "pharmaceutically effective amount" refers to an amount sufficient to treat a disease at a reasonable benefit or risk ratio, which is applicable to medical treatment. The pharmaceutically effective amount may be determined depending on factors including the disease type and severity of an individual, activity of drugs, sensitivity to drugs, time of administration, route of administration, excretion ratio, duration of treatment, and concurrently used drugs, and other factors well-known in the medical field.

Hereinafter, the present disclosure will be described in detail.

The present disclosure is characterized by providing a pharmaceutical composition containing, as an active ingredient, a strain having formic acid producing ability, a culture thereof, a lysate thereof, or an extract thereof for preventing or treating metabolic syndrome.

As cited herein, the "formic acid" is also called ant-acid or hydrogen carboxylic acid. The chemical formula is HCOOH. Formic acid has a molecular weight of 46.0, which is the smallest in carboxylic acids, and has a boiling point of 100.5° C., a melting point of 8.4° C., and a specific gravity of 1.220. Such formic acid is not only present in nature but also obtained from synthesis and is a fluidic and colorless liquid. The formic acid is slightly fumed when exposed to air and has irritating odor and corrosiveness. Formic acid is used in dyeing, tanning, coagulation of latex, or as a preservative in medicines or organic synthesis.

The formic acid according to the present disclosure may be in the form of a salt, preferably a pharmaceutically acceptable salt (formate).

The examples below of the present disclosure confirmed effects of reducing body weight, inhibiting fat accumulation in organ tissues, and lowering blood triglyceride and cholesterol levels according to the oral administration of a strain having excellent formic acid producing ability into obesity-induced animal models, and also, first confirmed that the size of epididymal fat cells was observed to be small in the groups orally administered with a strain having excellent formic acid producing ability.

Therefore, the present disclosure provides a composition containing, as an active ingredient, a strain having formic acid producing ability for preventing or treating obesity or metabolic syndrome.

As used herein, the "metabolic syndrome" may be a metabolic disease caused by obesity or a metabolic disease caused by any other cause. Examples of the metabolic syndrome may be selected from the group consisting of obesity, diabetes, arteriosclerosis, hypertension, hyperlipidemia, liver diseases, stroke, myocardial infarction, ischemic diseases, and cardiovascular diseases, but are not limited thereto.

As used herein, the "obesity" includes simple obesity, symptomatic obesity, child obesity, adult obesity, hyperplasia obesity, hypertrophic obesity, upper body obesity, lower body obesity, visceral fat obesity, and subcutaneous fat obesity, but is not limited thereto.

In an embodiment of the present disclosure, the strain having formic acid producing ability of the present disclosure may be at least one strain selected from the group consisting of *Enterococcus faecium* KR127 (accession number: KCTC 13135 BP), *Pediococcus pentosaceus* NKR654 (accession number: KCTC 13137 BP), and *Enterococcus faecalis* TN3 (accession number: KCTC 13136 BP).

The pharmaceutical composition of the present disclosure may be prepared by using a pharmaceutically acceptable and physiologically acceptable adjuvant in addition to the above-DOCS mentioned active ingredient, and examples of the adjuvant may be an excipient, a disintegrant, a sweetener, a binder, a coating agent, a swelling agent, a lubricant, a glydent, a flavoring agent, or the like.

The pharmaceutical composition, for administration, may be preferably formulated into a pharmaceutical composition by further containing at least one pharmaceutically acceptable carrier, in addition to the foregoing active ingredient.

The formulation form of the pharmaceutical composition may be granules, a powder, a tablet, a coated tablet, a capsule, a suppository, a liquid, syrup, juice, a suspension, an emulsion, drops, an injectable liquid, or the like. For example, for the formulation into a tablet or capsule, the active ingredient may be combined with an oral, non-toxic, pharmaceutically acceptable inert carrier, such as ethanol, glycerol, and water. Also, if desired or necessary, a suitable binder, a lubricant, a disintegrant, and a coloring agent may also be contained in the form of being mixed. The suitable binder includes, but is not limited to, natural sugars, such as starch, gelatin, glucose, or beta-lactose, corn sweeteners, natural and synthetic gums, such as acacia, tragacanth, or sodium oleate, sodium stearate, magnesium stearate, sodium benzoate, sodium acetate, sodium chloride, and the like. The disintegrant includes, but is not limited to, starch, methyl cellulose, agar, bentonite, xanthan gum, and the like. As for the composition formulated into a liquid solution, the pharmaceutically acceptable carrier is sterilizable and biocompatible, and may include saline, sterile water, Ringer's solution, buffered saline, an albumin injection solution, a dextrose solution, a maltodextrin solution, glycerol, ethanol, and a mixture of one or more thereof, and if necessary, other ordinary additives, such as an antioxidant, a buffer solution, and a bacteriostatic agent, may be added. In addition, the composition may be formulated into an injectable formulation, such as an aqueous solution, a suspension, or an emulsion, a pill, a capsule, granules, or a tablet by further adding to a diluent, a dispersant, a surfactant, a binder, and a lubricant thereto. Furthermore, the pharmaceutical composition may be preferably formulated according to the disease or ingredient by a suitable method in the art or using a method disclosed in Remington's Pharmaceutical Science, Mack Publishing Company, Easton Pa.

In an embodiment of the present disclosure, the strain having formic acid producing ability of the present disclosure may be contained in a content of $10^7$-$10^{12}$ cfu/g relative to a total weight of the composition.

Furthermore, the present disclosure provides a food composition containing, as an active ingredient, a strain having formic acid producing ability, a culture thereof, a lysate thereof, or an extract thereof for preventing or alleviating metabolic syndrome.

As used herein, the "metabolic syndrome" may be a metabolic disease caused by obesity or a metabolic disease caused by any other cause. Examples of the metabolic syndrome may be selected from the group consisting of obesity, diabetes, arteriosclerosis, hypertension, hyperlipidemia, liver diseases, stroke, myocardial infarction, ischemic diseases, and cardiovascular diseases, but are not limited thereto.

In an embodiment of the present disclosure, the strain having formic acid producing ability of the present disclosure may be at least one strain selected from the group consisting of *Enterococcus faecium* KR127 (accession number: KCTC 13135 BP), *Pediococcus pentosaceus* NKR654 (accession number: KCTC 13137 BP), and *Enterococcus faecalis* TN3 (accession number: KCTC 13136 BP).

According to an embodiment of the present disclosure, the strain having formic acid producing ability of the present disclosure can be used as a probiotic lactic acid bacteria or can be used in various dairy products and other fermented products, and can also be used as an animal feed additive.

The food composition is a food, a nutraceutical, a supplement, a probiotic, or a symbiotic.

As used herein, the term "food composition" refers to a food that provides a better health condition by advantageously acting on one or more functions of an organism regardless of the nutrients offered to a subject ingesting the food.

Consequently, the food composition can be used for prevention, alleviation, or treatment of a disease or a disease-inducing factor.

Therefore, the term "food composition" of the present disclosure may be used as a synonym of a functional food or a food or medicinal food for a specific nutritional purpose. As used herein, the term "probiotic" refers to live microorganisms that are beneficial to the health of a host organism when supplied in an appropriate amount. As used herein, the term "symbiotic" refers to a food containing a mixture of prebiotic and probiotic.

The food composition of the present disclosure may further contain at least one type of probiotic lactic acid bacteria selected from the group consisting of *Lactobacillus salivarius, Lactobacillus brevis, Lactobacillus helveticus, Lactobacillus fermentum, Lactobacillus paracasei, Lactobacillus casei, Lactobacillus delbrueckii, Lactobacillus reuteri, Lactobacillus buchneri, Lactobacillus gasseri, Lactobacillus johonsonii, Lactobacillus kefir, Lactococcus lactis, Bifidobacterium bifidum, Bifidobacterium infantis, Bifidobacterium pseudolongum, Bifidobacterium themophilum*, and *Bifidobacterium adolescentis*, in addition to the strain having formic acid producing ability of the present disclosure.

The strain having formic acid producing ability of the present disclosure can be collected after incubation and proliferation in a medium that is ordinarily used for the incubation of lactic acid bacteria under the conditions that are ordinarily employed. The culture obtained after incubation is used as it is, or further, as needed, subjected to rough purification by centrifugation or the like and/or solid-liquid separation or sterilization by filtration or the like. Preferably, only the cells of lactic acid bacteria are collected by centrifugation. In addition, the lactic acid bacteria used in the present disclosure may be wet cells or dry cells. For example, the lactic acid bacteria may be prepared as a biotic form by freeze-drying and then used.

The composition of the present disclosure may further contain, in addition to the active ingredient (the strain having formic acid producing ability, the culture thereof, the lysate thereof, or the extract thereof), an ordinary pharmaceutically acceptable carrier or excipient, and the composition may be prepared by formulation with, besides the above ingredients, various additives that are pharmaceutically and ordinarily used, such as a binder, a disintegrant, a coating agent, and a lubricant.

In an embodiment of the present disclosure, the strain having formic acid producing ability of the present disclosure may be contained in a content of $10^7$-$10^{12}$ cfu/g relative to a total weight of the food composition.

Besides containing the strain having formic acid producing ability, the culture thereof, the lysate thereof, or the extract thereof as an active ingredient, the food composition of the present disclosure, like ordinary food compositions, may contain various flavoring agents or natural carbohydrates as additional ingredients.

Examples of the foregoing natural carbohydrates may include ordinary sugars, such as monosaccharides (e.g., glucose and fructose); disaccharides (e.g., maltose and sucrose), and polysaccharides (e.g., dextrin and cyclodextrin); and sugar alcohols, such as xylitol, sorbitol, and erythritol. As the foregoing flavoring agents, natural flavoring agents (thaumatin), and *stevia* extracts (e.g., rebaudioside A, glycyrrhizin, etc.), and synthetic flavoring agents (saccharin, aspartame, etc.) may be advantageously used.

Furthermore, the food composition of the present disclosure may be preferably formulated into a food composition by further containing at least one sitologically acceptable or pharmaceutically acceptable carrier, in addition to the foregoing active ingredient (the strain having formic acid producing ability, the culture thereof, the lysate thereof, or the extract thereof).

The formulation form of the food composition may be a tablet, a capsule, a powder, granules, a liquid, a pill, a liquid preparation, syrup, juice, a suspension, an emulsion, drops, or the like. For example, for the formulation into a tablet or capsule, the active ingredient may be combined with an oral, non-toxic, pharmaceutically acceptable inert carrier, such as ethanol, glycerol, and water. Also, if desired or necessary, a suitable binder, a lubricant, a disintegrant, and a coloring agent may also be contained in the form of being mixed. The suitable binder includes, but is not limited to, natural sugars, such as starch, gelatin, glucose, or beta-lactose, corn sweeteners, natural and synthetic gums, such as acacia, tragacanth, or sodium oleate, sodium stearate, magnesium stearate, sodium benzoate, sodium acetate, sodium chloride, and the like. The disintegrant include, but is not limited to, starch, methyl cellulose, agar, bentonite, xanthan gum, and the like. As for the composition formulated into a liquid solution, the pharmaceutically acceptable carrier is sterilizable and biocompatible, and may include saline, sterile water, Ringer's solution, buffered saline, an albumin injection solution, a dextrose solution, a maltodextrin solution, glycerol, ethanol, and a mixture of one or more thereof, and if necessary, other ordinary additives, such as an antioxidant, a buffer solution, and a bacteriostatic agent, may be added. In addition, the food composition may be formulated into an injectable formulation, such as an aqueous solution, a suspension, or an emulsion, a pill, a capsule, granules, or a tablet by further adding to a diluent, a dispersant, a surfactant, a binder, and a lubricant thereto.

The food composition of the present disclosure formulated in the above-described manners can be used as a functional food or added to various foods.

Exemplary foods to which the composition of the present disclosure is addable may include, for example, drinks, meats, chocolates, foods, confectionery, pizzas, ramen, other noodles, gums, candies, ice creams, alcohol drinks, vitamin complexes, health supplement foods, and the like.

In addition, the food composition may contain, in addition to the active ingredient (the strain having formic acid producing ability, the culture thereof, the lysate thereof, or the extract thereof), various nutrients, vitamins, minerals (electrolytes), flavoring agents, such as synthetic flavoring agents and natural flavoring agents, coloring agents, extenders (cheese, chocolate, etc.), pectic acid and salts thereof, alginic acid and salts thereof, organic acids, protective colloidal thickeners, pH adjusters, stabilizers, preservatives, glycerin, alcohols, carbonating agents used for carbonated drinks, and the like. Besides, the food composition of the present disclosure may contain fruit flesh for manufacturing natural fruit juice, fruit juice drinks, and vegetable drinks.

The strain having formic acid producing ability as an active ingredient of the present disclosure is a food-derived bacterium, but is a species that is frequently found in the intestine. The stain has excellent effects of reducing body weight, inhibiting fat accumulation in organ tissues, and lowering blood triglyceride and cholesterol levels, and thus can be safely used without few side effects in chemicals even in the long-term taking for the purpose of providing functionality, such as anti-obesity or alleviation of metabolic symptoms.

Furthermore, the present disclosure provides a health functional food containing, as an active ingredient, a strain having formic acid producing ability, a culture thereof, a lysate thereof, or an extract thereof for preventing or alleviating metabolic syndrome.

In an embodiment of the present disclosure, the strain having formic acid producing ability of the present disclosure may be at least one strain selected from the group consisting of *Enterococcus faecium* KR127 (accession number: KCTC 13135 BP), *Pediococcus pentosaceus* NKR654 (accession number: KCTC 13137 BP), and *Enterococcus faecalis* TN3 (accession number: KCTC 13136 BP).

The health functional food of the present disclosure may be manufactured and processed in the form of a tablet, a capsule, a powder, granules, a liquid, a pill, or the like, for the purpose of prevention or alleviation of metabolic syndrome.

As used herein, the term "health functional food" refers to a food that is manufactured and processed by using raw materials or ingredients having functionality useful to the human body according to the Korean Health/Functional Food Act, and means one that is taken for the purpose of obtaining effects useful for regulating nutrients for the structure and function of the human body or for obtaining effects useful for hygienic purposes such as a physiological action.

The health functional food of the present disclosure may contain ordinary food additives, and the suitability thereof as a food additive, unless otherwise specified, is determined by the standards and criteria for a corresponding item according to the general provisions of Korean Food Additives Codex and General Test Method approved by the Korean Food and Drug Administration.

Examples of the items listed on the "Korean Food Additives Codex" may include: chemical synthetic products, such as ketone, glycine, potassium citrate, nicotinic acid, and cinnamic acid; natural additives, such as persimmon color, a licorice root extract, crystalline cellulose, Kaoliang color, and guar gum; and mixed preparations, such as sodium L-glutamate preparations, an alkali agent for noodles, a preservative preparation, and a tar color formulation.

For example, as for a tablet form of health functional food, a mixture obtained by mixing the active ingredient (the strain having formic acid producing ability, the culture thereof, the lysate thereof, or the extract thereof) of the present disclosure with an excipient, a binder, a disintegrant, and other additives is granulated by an ordinary method, and then a glydent and the like is added thereto, followed by compressive molding, or the mixture is directly compressive molded. The tablet form of health functional food may contain a sour taste agent and the like as necessary.

Out of the capsule form of health functional foods, a hard capsule may be manufactured by filling an ordinary hard capsule with the active ingredient (the strain having formic acid producing ability, the culture thereof, the lysate thereof, or the extract thereof) of the present disclosure, and a soft capsule may be manufactured by filing a capsule, such as gelatin, with a mixture obtained by mixing the formic acid and an additive, such as an excipient. The soft capsule may contain a plasticizer, a coloring agent, a preservative, or the like, such as glycerin or sorbitol, as necessary.

A pill form of health functional food may be manufactured by molding a mixture of the active ingredient (the strain having formic acid producing ability, the culture thereof, the lysate thereof, or the extract thereof) of the present disclosure with an excipient, a binder, a disintegrant, and the like through an existing known method, and as necessary, the pill form of health functional food may be coated with white sugar or another coating agent, or a surface thereof may be coated with a material, such as starch or talc.

A granule form of health functional food may be manufactured by granulating a mixture of the active ingredient (the strain having formic acid producing ability, the culture thereof, the lysate thereof, or the extract thereof) of the present disclosure with an excipient, a binder, a disintegrant, and the like through an existing known method, and the granule form of health functional food may contain a coloring agent, a sour taste agent, or the like, as necessary.

The health functional food may include drinks, meats, chocolates, foods, confectionery, pizzas, ramen, other noodles, gums, candies, ice creams, alcohol drinks, vitamin complexes, and health supplement foods.

Hereinafter, the present disclosure will be described in detail with reference to examples. However, these examples are given for specifically illustrating the present disclosure, and the scope of the present disclosure is not limited thereto.

MODE FOR CARRYING OUT THE INVENTION

EXAMPLES

Statistics

For statistical analysis of fecal organic acids in an obesity group and a normal control group, the system Statistical Package for Social Science (SPSS, SPSS Inc., Chicago, Ill., USA) software package (version 12.0) was used, and a significant difference between samples was analyzed by T-test at a level of $p<0.05$. The statistical analysis of body weight, organ weights, and blood was conducted using SPSS system (statistical Package For Social Science, SPSS Inc., Chicago, Ill., USA) software package (version 12.0), and a significant difference between samples was analyzed by Duncan's multiple range test at a level of $p<0.05$.

Example 1

Collection of Feces and Analysis of Organic Acids in Normal Control Group and Obesity Group The feces of a normal control group (n=33) and an obesity group (n=44) both of males in their 50s used in this study were samples that had been obtained from the Catholic University, Seoul Catholic Hospital (Seocho, Korea) through IRB deliberation (IRB acquisition at Seoul Catholic Hospital: KC14TIS10325). Analysis of organic acids in the feces were conducted by the National Instrumentation Center for Environmental Management (NICEM, Korea), Seoul National University. For analysis of organic acids, each sample was 10-fold diluted with tertiary distilled water, centrifuged at 3000 rpm for 10 min, and then subjected to filtration using a 0.22 μm-membrane filter, and thus was used as a sample for HPLC (Ultimate3000, Dionex, USA) analysis. The HPLC column used was an Aminex 87H column (300×7.8 mm), and the temperature was maintained at 40° C. The mobile phase was allowed to flow at a rate of 0.5 ml/min using 0.01 N $H_2SO_4$. A single injection of the sample was 10 μl, and was analyzed for 30 min using the detector RI (Shodex RI-101, Japan) and UV (210 nm).

As a result, as shown in Table 1 below, the organic acids detected commonly in normal people and obese people were formic acid, acetic acid, and butyric acid. The content of formic acid was 0.22 mMol in the normal control group, which was 2.4-fold higher compared with the obesity group, indicating a significant difference. The contents of acetic acid and butyric acid in the normal control group were 0.9-fold and 0.8-fold compared with the obesity group, respectively.

Meanwhile, such content differences were obtained from the analysis results including the patients with diabetes, obesity, hypertension, and hyperlipidemia, greatly associated with obesity, and thus analysis was again conducted excluding these patients.

As a result, as shown in Table 2 below, the formic acid was 0.27 mMol in the normal control group, which was about 6.8-fold higher compared with the obesity group, indicating a significant difference. Whereas, the contents of acetic acid and butyric acid in the normal control group were 0.82-fold and 0.66-fold compared with the obesity group, respectively, but such data indicated no significant difference, and propionic acid was detected in neither the normal control group nor the obesity group.

TABLE 1

Comparison of average values of fecal organic acids between obesity group and normal control group

| Sample | Organic acid content (mMol) | | | |
|---|---|---|---|---|
| | Formic acid | Propionic acid | Acetic acid | Butyric acid |
| Normal control group [N = 33] | 0.22 ± 2.29[1),2)] | ND[3)] | 8.72 ± 3.76[a] | 2.17 ± 1.49[a] |
| Obesity group [N = 44] | 0.09 ± 0.14[B] | ND | 9.98 ± 2.69[a] | 2.88 ± 1.89[a] |

[1)]Each value represents the mean ± S.D. for groups.
[2)]Means followed by the same letter in the column are not significantly different (p < 0.05)
[3)]ND; not detected

TABLE 2

Comparison of average values of fecal organic acids between obesity group and normal control group excluding disease patients (any one of obesity, hypertension, and hyperlipidemia

| Sample | Organic acid content (mMol) | | | |
|---|---|---|---|---|
| | Formic acid | Propionic acid | Acetic acid | Butyric acid |
| Normal control gorup [N = 23] | 0.27 ± 0.31[1),2)] | ND[3)] | 8.72 ± 3.73[A] | 2.30 ± 1.59[A] |
| Obesity group [N = 21] | 0.04 ± 0.09[B] | ND | 10.60 ± 2.58[A] | 3.46 ± 2.42[A] |

[1)]Each value represents the mean + S.D. for groups.
[2)]Means followed by the same letter in the column are not significantly different (p < 0.05)
[3)]ND; not detected It was confirmed through the above results that out of the organic acids detected in feces, only formic acid was significantly higher in the normal control group compared with the obesity group. Therefore, formic acid was thought to have an anti-obesity effect in the intestinal environment.

For reference, the results of the present disclosure as described above are meaningful in that the results were derived from the feces of Korean males in their 50s. The reason is that the conventional obesity studies were conducted not on Korean-customization, but on other races or ethnic groups, and also, as for the target age for obesity studies, the results optimized for adult obesity could not be deduced when obesity studies were not conducted on adults (obesity studies were conducted on infants and adolescents). The human physiology is different between the adolescence and menopause, and it is well known that the fecal bacteria flora is also greatly different between children and adults, and thus it is obvious that the resultant fecal metabolites are different therebetween.

Hence, it was meaningful in that for the conduction of research optimized for Korean adult obesity, the present inventors examined differences between normal adults and obese adults in Korean adults in their 50s through fecal collection and organic acid analysis, and therefore first discovered a factor having a direct correlation with Korean adult obesity.

In order to investigate whether formic acid actually has an anti-obesity effect, the present inventors orally administered formate into high-fat diet-induced obesity animal models. As a result, it was confirmed through an objective experiment that, in the formate oral administration experimental group compared with the high-fat diet control group, the body weight increase was inhibited, the kidney fat weight value was lowered, the blood triglyceride and cholesterol contents were significantly reduced, and the fat cell size was decreased. The patent application procedure of the above-described contents is under way, separately from the present disclosure.

Also, in order to investigate whether the intake of, as a probiotic, a strain producing a lot of formic acid actually shows an anti-obesity effect on the basis of the above results, the present inventors selected a total of three species of novel strains producing a lot of formic acid in the following experiment, and conducted an animal experiment to investigate an anti-obesity effect according to the feeding of the above strains as a probiotic into obesity animal models.

Example 2

Preparation and Selection of Experimental Strains

In order to select superior strains producing formate, the absorbance values of broths, which contain 30 species of intestinal microorganisms and food-derived bacteria incubated therein and are stored in the present laboratory, were measured at 660 nm using an absorption spectrophotometer. At a measurement value of about 1.4, 1 mL of each culture fluid was centrifuged (7000 rpm, 1 min) using a centrifuge, and then the supernatant was taken, filtered through a 0.22 µm-nylon syringe filter, and subjected to organic acid analysis.

Table 3 below shows the comparisons of the amounts of organic acids (lactic acid, propionic acid, acetic acid, and formic acid) produced by each of 30 species of strains.

TABLE 3

Comparison of organic production by 30 species of strains (mMol)

| Strain name | Butyric acid | Propionic acid | Acetic acid | Formic acid |
|---|---|---|---|---|
| Enterococcus faecalis TN3 | ND[1] | ND. | 10.73 | 2.16 |
| Pediococcus pentosaceus NKR654 | ND | 1.02 | 13.3 | 2.41 |
| Enterococcus faecium KR127 | ND | 3.11 | 17.28 | 6.72 |
| Bifidobacterium Bifidum KFRI743 | ND | ND | 18.12 | ND |
| Bacteroides fagilis KCTC3688 | ND | ND | 18.96 | ND |
| Weissella halotolerans KCTC3595 | ND | ND | 15.48 | ND |
| Lactobacillus bifermentans KFRI1030 | ND | 2.3 | 14.25 | ND |
| Klebsiella pneumoniae U12 | ND | 6.29 | 18.03 | ND |
| Bacillus thuringiensis KFRI550 | ND | 4.47 | 8.64 | ND |
| Weissella parameseentefoides KCTC3531 | ND | ND | 10.23 | ND |
| Bacillus coagulans M46 | ND | 1.6 | 7.12 | 0.96 |
| Leuconostoc kimchi KCCM41287 | ND | 2.89 | 6.03 | ND |
| Lactobacillus paracasei KFRI818 | ND | 2.68 | 8.7 | ND |
| Weissella hellenica KCTC3668 | ND | 1.61 | 7.22 | ND |
| Bacteroides uniformis KCTC5204 | ND | 0.74 | 19.62 | ND |
| Leuconostoc paramesenteroides KL4 | ND | ND | 8.79 | ND |
| Lactobacillus fermentum KFRI657 | ND | ND | 8.18 | ND |
| Leuconostoc pseudomesenteroides KCTC3652 | ND | ND | 8.43 | ND |
| Weissella kimchi KCCM41287 | ND | 0.71 | 8.8 | ND |
| Pediococcus dextranicum WP3 | ND | 2.61 | 16.04 | ND |
| Weissella koreensis D2-332 | ND | 2.44 | 11.57 | ND |
| Lactobacillus acidophilus KFRI340 | ND | 0.39 | 5.23 | ND |
| Leuconostoc fallax GS2-1 | ND | ND | 7.62 | ND |
| Staphylococcus warneri IO2-10 | ND | 6.45 | 18.63 | ND |
| Escherichia coli SKD4008 | ND | ND | 17.03 | ND |
| Enterococcus solitaries KCTC3553 | ND | 1.96 | 11.02 | 0.93 |
| Weissella viridescens KFRI184 | ND | ND | 14.01 | ND |
| Staphylococcus saprophyticus AT7 | ND | 1.88 | 6.11 | ND |
| Eubacterium multiforme KCTC15004 | ND | ND | 16.48 | 0.76 |
| Bacillus aerophilus IM1-17 | ND | 6.25 | 16.33 | ND |

[1]ND; not detected

As a result, it was observed as shown above that *Enterococcus faecalis* TN3 produced 2.16 mmol of formic acid; *Pediococcus pentosaceus* NKR654 produced 2.41 mmol of formic acid; and *Enterococcus faecium* KR127 produced 6.72 mmol of formic acid. While, no formic acid or an extremely small amount of formic acid was detected in 27 species of strains except the above strains.

For reference, the three species of strains showing predominant production of formate are novel strains that were purely separated from tradition food materials (nuruk, kimchi, and cheese) by the present inventors and identified through 16S rDNA region Sequencing Analysis by Macrogen Inc., and were named "*Enterococcus faecalis* TN3", "*Pediococcus pentosaceus* NKR654", and "*Enterococcus faecium* KR127", respectively.

The 16S rDNA region sequencing method used by Macrogen is briefly as follows. That is, strain genomic DNA samples were extracted using InstaGenetm Matrix (BIO-RAD.), and then PCR was performed using 27F 5' (AGA GTT TGA TCM TGG CTC AG) 3' and 1492R 5' (TAC GGY TAC CTT GTT ACG ACT T) 3' as primers. The PCR reaction was performed with 20 ng of genomic DNA as the template strand in a 30 µL reaction mixture by using a EF-Taq (SolGent, Korea) (reaction conditions: activation of Taq polymerase at 95° C. for 2 minutes, 35 cycles of 95° C. for 1 minutes, 55° C., and 72° C. for 1 minutes each were performed, finishing with a 10-minute step at 72° C.). The amplification products were purified with a multiscreen filter plate (Millipore Corp., Bedford, Mass., USA).

Sequencing reaction was performed using PRISM Big-Dye Terminator v3.1 Cycle sequencing Kit. Hi-Di formamide (Applied Biosystems, Foster City, Calif.) was added to the DNA samples containing extension products. The mixture was incubated at 95° C. for 5 min, followed by 5 min on ice, and then analyzed by ABI Prism 3730XL DNA analyzer (Applied Biosystems, Foster City, Calif., USA).

The three species of selected strains showing predominant production of formate were deposited at the KCTC (Korean Collection for Typo Cultures) on 18 Oct. 2016 and assigned accession numbers KCTC 13135BP, KCTC 13136BP, and KCTC 13137BP, respectively.

The three species of strains showing predominant production of formate were used in the animal experiments below.

Example 3

Preparation of Obesity Animal Models

<3-1> Experimental Animals and Diet

In the present experiment, five-week-old C57BL/6J mice were purchased from Saeron Bio (Uiwang, Korea), and acclimated for 1 week before use in the experiment. The rearing room was controlled to have a temperature of 20±2° C., a humidity of 55±10%, and a light/darkness cycle of 12 hours during the experimental period. The experimental animals were divided into 5 groups according to the randomized block design, after 1-week of normal diet. The experimental groups were classified into Group A (normal diet group; n=10), Group B (high-fat diet control group; n=10), Group C (high-fat diet+*Enterococcus faecium* ($10^9$ CFU/g/day); n=8), Group D (high-fat diet+*Pediococcus pentosaceus* ($10^9$ CFU/g/day); n=8), and Group E (high-fat diet+*Enterococcus faecalis* ($10^9$ CFU/g/day); n=9).

<3-2> Treatment of Experimental Animals

Water and feed were freely accessible. Groups A and B were orally administered with physiological saline, and the other groups were orally administered with corresponding strain-diluted liquids once a day (2 µg/g bodyweight). For the test groups, obesity was induced by a high-fat diet for 13 weeks, and a high-fat diet (D12492; 60% of the calories) purchased from Research Diet (USA) was used in the experiment. All animal experiments in the present study were conducted under the approval (KFRI-M-16043(263)) of the Institutional Animal Care and Use Committee (IACUC) of the Korea Food Research Institute.

Example 4

Body and Organ Weight Measurement and Blood Analysis in Experimental Animals

The body weights of the experimental animals were measured at a fixed time once a week during the experiment. The experimental animals were fasted for 12 hours before sacrifice, and blood was collected from eyes of the experimental animals anesthetized with ether. In order to prevent the coagulation of the blood after collection, the blood was placed in anti-coagulation tubes and left in an ice bath for 20 min. The collected blood samples were centrifuged at 3000 rpm for 10 min to separate serum therefrom, and refrigerated until use in the experiment. Thereafter, the kit through an enzymatic method was purchased from Young Dong Diagnostics (Yong-In, Korea) to measure the levels of blood lipids (triglyceride, cholesterol, HDL-Cholesterol, and LDL-Cholesterol). The organs were extracted, washed with physiological saline, dehydrated with a filter bed, and then weighed.

<4-1> Body Weight Change

The cells of *Enterococcus faecium* KR127 (KCTC13135BP), *Pediococcus pentosaceus* NKR654 (KCTC13137BP), and *Enterococcus faecalis* TN3 (KCTC13136BP) were diluted with physiological saline, and orally administered to high-fat diet-induced obesity animal models (C57BL/6J mice) for 13 weeks. The mouse body weight measurement was conducted once a week during the time of rearing, and the resulting body weight changes were determined.

As a result, as shown in FIG. 1, the average weight after 13 weeks of rearing was 31.00 g in Group A (normal diet control group), 41.09 g in Group B (high-fat diet control group), 35.67 g in Group C (oral administration with the strain *Enterococcus faecium* KR127 (KCTC13135BP), $10^9$ CFU/g/day), 40.33 g in Group D (oral administration with the strain *Pediococcus pentosaceus* NKR654 (KCTC13137BP), $10^9$ CFU/g/day), and 41.38 g in Group E (oral administration of the strain *Enterococcus faecalis* TN3 (KCTC13136BP), $10^9$ CFU/g/day). Resultantly, Group C significantly showed a 13.19% lower value compared with the high-fat diet control group. Groups D and E showed similar values to the high-fat diet control group, indicating no significant difference.

It was thought through the present experiment that the strain *Enterococcus faecium* KR127 (KCTC13135BP) producing a lot of formate was most effective in the inhibition of body weight increase and anti-obesity.

<4-2> Effect on Organ Weights

High-fat diet feeding greatly increases the weights of liver fat and epididymal fat in white mice (Handjieva-Daelenska T, Boyajieva N. 2009). The intake of high-fat diet for a long time brings fat into the blood, inducing fat accumulation in the liver. The high-fat diet causes the imbalance in glucose metabolism, thereby increasing glucose uptake, resulting in abnormality in the liver (Buettner R et al. 2006, Gregoire F M. 2002). The epididymal fat is white fat resulting from the storage of excess energy into fat in the body, and causes metabolic changes, such as blood lipid contents, as main indicators of visceral obesity in mice (Avram A S et al 2005, Handgieva-Daelenska T et al. 2007). The kidney fat, epididymal fat, subcutaneous fat, brown fat, prostate, liver, and spleen were extracted immediately after blood collection from the control and experimental groups, and washed with physiological saline, subjected to surface moisture removal, and then weighed. The results are shown in Table 4 below.

The weight of kidney fat was significantly higher in the high-fat diet control group (0.84±0.12 g) rather than the normal diet control group (0.43±0.14 g), and the weights of kidney fat in Groups C, D, and E were 0.69 g, 0.74 g, and 0.82 g, respectively. Compared with the high-fat diet control group, only Group C showed a significantly low value (p<0.05), and Groups D and E showed lower values, indicating no significant difference. The reason was thought that the feeding of the strain *Enterococcus faecium* KR127 (KCTC13135BP) would inhibit the accumulation of kidney fat.

The weight of epididymal fat was observed to be more affected by diet than the weights of the other types of fat.

All the strain treatment groups (Groups C, D, and E) showed lower values compared with the high-fat diet control group (Group B), while group C showed an 18.4% lower value, Group D 15.2%, and Group E 4%. The group administered with *Enterococcus faecium* KR127 (KCTC13135BP) showed a significant low value.

The weight of subcutaneous fat was also observed to be greatly affected by diet, while Group C showed 1.32 g, Group D 1.58 g, and Group E 1.74 g. Compared with the high-fat diet control group, Group C showed a 16.46% lower value, indicating no significant difference, and Groups D and E also showed no significant difference. It was thought that the feeding of the strain *Enterococcus faecium* KR127 (KCTC13135BP) would inhibit fat accumulation in kidney fat and epididymal fat.

As for the weight of brown fat, all the strain treatment groups (Groups C, D, and E) showed a 22.22% higher value compared with the high-fat diet control group (Group B), indicating no significant difference, and therefore, the brown fat was considered to be an organ less affected by diet.

There was about a 1.9-fold difference in weight of the prostate between the normal diet control group and the high-fat control diet group, and the prostate was observed to be a tissue greatly affected by diet. The weight of prostate was higher in Group C compared with the high-fat diet control group, indicating no significant difference.

The weight of liver and the weight of spleen also showed no significant difference among the groups. From the results of epididymal fat weight in mice, which is considered to be a main indicator of visceral obesity, it would thought that the administration of the strain *Enterococcus faecium* KR127 (KCTC13135BP) producing a lot of formate was effective in body weight loss and anti-obesity.

TABLE 4

Measurement of weights of mouse organs in each group
(Unit: g)

| Group | Kidney fat | Epididymal fat | Subcutaneous fat | Brown fat | Prostate | Liver | Spleen | Bone |
|---|---|---|---|---|---|---|---|---|
| A[1)] (n = 10) | 0.43 ± 0.142$^C$ | 1.12 ± 0.24$^C$ | 0.65 ± 0.16$^B$ | 0.09 ± 0.03$^A$ | 0.10 ± 0.04$^B$ | 0.93 ± 0.12$^A$ | 0.06 ± 0.01$^A$ | 15.45 ± 0.41$^A$ |
| B (n = 10) | 0.84 ± 0.12$^A$ | 2.50 ± 0.48$^A$ | 1.58 ± 0.39$^A$ | 0.09 ± 0.03$^A$ | 0.19 ± 0.07$^A$ | 0.96 ± 0.12$^A$ | 0.07 ± 0.01$^A$ | 15.21 ± 0.35$^A$ |
| C (n = 9) | 0.69 ± 0.06$^B$ | 2.04 ± 0.41$^B$ | 1.32 ± 0.21$^A$ | 0.11 ± 0.02$^A$ | 0.23 ± 0.04$^A$ | 0.92 ± 0.10$^A$ | 0.07 ± 0.01$^A$ | 15.35 ± 0.36$^A$ |
| D (n = 9) | 0.74 ± 0.16$^{AB}$ | 2.12 ± 0.52$^{AB}$ | 1.58 ± 0.65$^A$ | 0.11 ± 0.03$^A$ | 0.21 ± 0.06$^A$ | 1.02 ± 0.32$^A$ | 0.06 ± 0.01$^A$ | 15.31 ± 0.27$^A$ |
| E (n = 8) | 0.82 ± 0.11$^A$ | 2.40 ± 0.43$^{AB}$ | 1.74 ± 0.47$^A$ | 0.11 ± 0.04$^A$ | 0.21 ± 0.04$^A$ | 0.96 ± 0.23$^A$ | 0.06 ± 0.01$^A$ | 15.22 ± 0.26$^A$ |

[1)A]normal diet group,
[B]high fat diet group,
[C]high fat diet group with *Enterococcus faecium* KR127,
[D]high fat diet group with *Pediococcus pentosaceus* NKR654
[E]high fat diet group with *Enterococcus faecalis* TN3
[2)]Each value represents the mean ± S.D. for groups.
[3)]Means followed by the same letter in the column are not significantly different (p < 0.05)

<4-3> Blood Analysis

Obesity is often accompanied by abnormal dyslipidemia due to abnormal lipid metabolism and glucose metabolism. Lee et al. and Jang and Choi reported that the blood triglyceride and cholesterol levels increased and the HDL-cholesterol level decreased in white mice with high-fat diet-induced obesity.

The effects of the administration of *Enterococcus faecium* KR127 (KCTC13135BP), *Pediococcus pentosaceus* NKR654 (KCTC13137BP), and *Enterococcus faecalis* TN3 (KCTC13136BP) on serum lipid concentrations are shown in Table 5 below.

The serum triglyceride (TG) concentration was 86.64±4.21 mg/dL in the normal diet group (A), but 130.10±7.69 mg/dL in the high-fat diet control group (B), showing a higher concentration compared with the normal diet group. The *Enterococcus faecium* KR127 (KCTC13135BP) administration group (C) showed 98.89±7.14 mg/dL, corresponding to a 23.99% lower value compared with the high-fat diet control group. The *Pediococcus pentosaceus* NKR654 (KCTC13137BP) administration group (D) showed 148.33±8.35 mg/dL, and the *Enterococcus faecalis* TN3 (KCTC13136BP) administration group (E) showed 145.45±4.96 mg/dL. It was thought from such results that the reduction of blood triglyceride concentration was affected by the administration of *Enterococcus faecium* KR127 (KCTC13135BP).

The content of cholesterol was increased by 61.2% in the high-fat diet feeding control group compared with the normal diet group (A), and was significantly reduced in the administration of the strains compared with the high-fat diet feeding control group. Group C (*Enterococcus faecium* KR127 (KCTC13135BP) administration group) showed a 36.8% lower value compared with the high-fat diet control group, and Group D 29.67%, and group E 37.64%.

HDL-cholesterol, which is an indicator of anti-arteriosclerosis, has a protective action against coronary heart disease by transporting cholesterol from peripheral blood vessels to the liver to deliver arteriosclerosis in a direction that does not progress arteriosclerosis. The HDL-cholesterol concentration in the present experiment was observed to show a significantly lower value in the strain administration groups compared with the high-fat diet group (B).

LDL-cholesterol is a main delivery type for blood cholesterol. LDL-cholesterol accumulates cholesterol on the arterial vascular walls to accelerate arteriosclerosis, and thus there is a close correlation between the concentration of blood LDL-cholesterol and the occurrence of cardiocirculatory diseases. The content of LDL-cholesterol was 23.62% higher in the high-fat diet control group (B) compared with the normal diet group (A). Out of the strain administration groups, Group D showed a lower value compared with the high-fat diet control group.

TABLE 5

Measurement of serum lipid concentrations
in mice of each group (Unit: mg/dl)

| Group | Cholesterol | Triglyceride | HDL | LDL |
|---|---|---|---|---|
| A[1)] | 77.29 ± 9.69$^C$ | 86.64 ± 4.21$^D$ | 52.73 ± 1.19$^B$ | 22.27 ± 0.39$^C$ |
| B | 124.59 ± 9.45$^A$ | 130.10 ± 7.69$^A$ | 61.09 ± 1.36$^A$ | 27.53 ± 1.69$^B$ |
| C | 78.80 ± 2.94$^C$ | 98.89 ± 7.12$^C$ | 44.11 ± 3.53$^C$ | 31.32 ± 1.04$^A$ |
| D | 87.62 ± 3.24$^B$ | 148.33 ± 8.35$^B$ | 41.03 ± 0.89$^D$ | 23.73 ± 1.25$^C$ |
| E | 77.69 ± 3.25$^C$ | 145.45 ± 4.96$^B$ | 41.29 ± 0.72$^D$ | 29.83 ± 1.03$^A$ |

[1)A]normal diet group,
[B]high fat diet group,
[C]high fat diet group with Enterococcus faecium KR127,
[D]high fat diet group with Pediococcus pentosaceus NKR654
[E]high fat diet group with Enterococcus faecalis TN3
[2)]Each value represents the mean ± S.D. for groups.
[3)]Means followed by the same letter in the column are not significantly different (p < 0.05)

From the above results, the contents of triglyceride and total cholesterol in lipids, which are the causative substances of adult diseases, were reduced by the administration of *Enterococcus faecium* KR127 (KCTC13135BP), and thus it was thought that *Enterococcus faecium* KR127 (KCTC13135BP) will be effective in anti-obesity and the prevention of cardiovascular diseases caused by the intake of fat diet.

Example 5

Size Measurement of Epididymal Fat Cells

For size measurement of epididymal fat cells, the epididymal fat tissue extracted according to the method by Hirsch and Gallian (Hirsch, J. and Gallian, E. 1968. Methods for the determination of adipose cell size in man and animals. J. Lipid Res. 9:110-119) was immobilized with 10% formalin, and passed through a 250 μm-nylon filter to remove fibrous tissues and small tissues, and then washed with PBS to completely the tissues. The immobilized tissue was sliced into 18 μm using a cryostat microtome, and fat cells were stained by hematoxylin and eosin (H&E) fat staining. The fat cells were decolorized using 60% isopropanol after the staining, and then imaged using a digital camera under a microscope. For size analysis of fat cells, the area of fat cells was measured using Image J Software (National Institute of Health, Maryland, USA).

For reference, the measurement of fat cell size is known to be an effective method to demonstrate anti-obesity efficacy, and the intake of high-fat diet increases the accumulation of triglyceride in fat cells, thereby increasing the size of fat cells (Park, S. H., Ko, S. K. and Chung, S. H. 2005. *Euonymus alatus* prevents the hyperglycemia and hyperlipidemia induced by high-fat diet in ICR mice. J. Ethnophamacol. 102:326-335).

Figure 2:
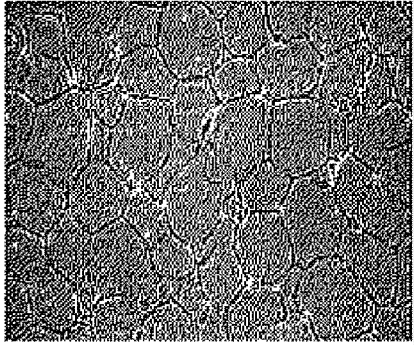
FIG. 2 shows images illustrating sizes of epididymal fat issue cells according to the feeding of various strains to high-fat diet-induced obesity experimental animals (A: normal diet group, B: high-fat diet group, C: high-fat diet+*Enterococcus faecium* KR127 feeding group, D: high-fat diet+*Pediococcus pentosaceus* NKR654 feeding group, E: high-fat diet+*Enterococcus faecalis* TN3 feeding group).
Figure 2:
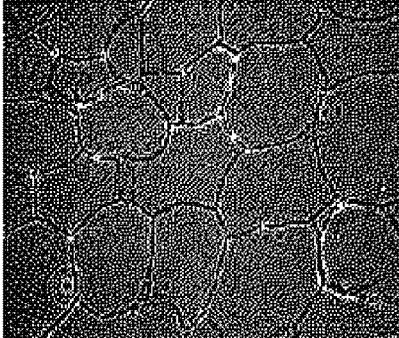
Figure 2:
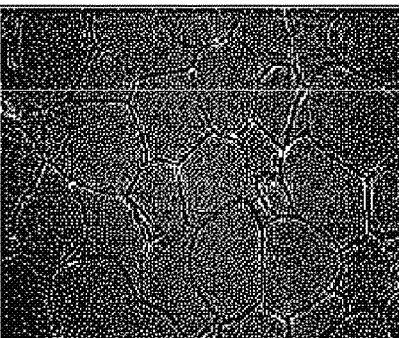
Figure 2:
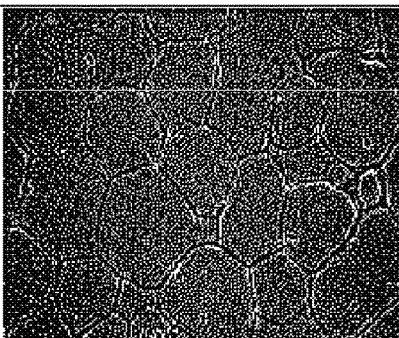
Figure 2:
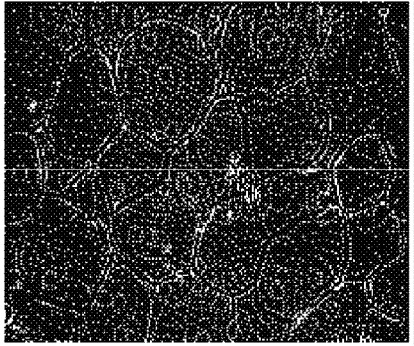

The size measurement results of epididymal fat cells through the present experiment are shown in FIG. 2. From the result of average area distribution of fat cells, Group B had the largest fat cell size, 4600.18 µm$^2$, which were 55.9% higher compared with Group A. The size of fat cells was smallest in the *Pediococus pentosaceus* NKR654 (KCTC13137BP) oral administration group, and was larger in the *Enterococcus faecium* KR127 (KCTC13135BP) oral administration group and the *Enterococcus faecalis* TN3 (KCTC13136BP) oral administration group in that order. Considering that all the strain administration groups showed smaller fat cell sizes compared with the high-fat diet control group, it was thought that the feeding of the strains would inhibit the accumulation of fat cells caused by high-fat diet. When the fat cells stained with H&E were observed under a microscope, the differences in fat cell size could also be seen by the naked eyes.

More research will be needed in the future, but as examined above, the possibility is suggested that out of the strain treatment groups, the strain *Enterococcus faecium* KR127 (KCTC13135BP) producing a lot of formate can be developed as an agent having an anti-obesity effect and alleviating hyperlipidemia.

As set forth above, the present disclosure has been described with reference to preferable embodiments. Those skilled in the art to which the present disclosure pertain would understand that the present disclosure could be implemented in a modified form without departing from the inherent characteristics of the present disclosure. Accordingly, the embodiments described herein should be considered from an illustrative aspect rather than from a restrictive aspect. The scope of the present disclosure should be defined not by the detailed description but by the appended claims, and all differences falling within a scope equivalent to the claims should be construed as being included in the present disclosure.

INDUSTRIAL APPLICABILITY

The strain having formic acid producing ability according to the present disclosure can be helpfully used as a substance for medical products or health foods.

[Accession numbers]
Depository authority: Korean Collection for Type Cultures
Accession number: KCTC13135BP
Deposit date: 18 Oct. 2016
Depository authority: Korean Collection for Type Cultures
Accession number: KCTC13136BP
Deposit date: 18 Oct. 2016
Depository authority: Korean Collection for Type Cultures
Accession number: KCTC13137BP
Deposit date: 18 Oct. 2016

The invention claimed is:

1. A method of preventing or treating metabolic syndrome in a mammal in need thereof, said method comprising:
   administering to the mammal in need thereof a strain having formic acid producing ability,
   wherein the strain is at least one species selected from the group consisting of *Enterococcus faecium* KR127 (accession number: KCTC 13135 BP), *Pediococcus pentosaceus* NKR654 (accession number: KCTC 1313 7 BP), and *Enterococcus faecalis* TN3 (accession number: KCTC 13136 BP).

2. The method of claim 1, wherein the metabolic syndrome is selected from the group consisting of obesity, diabetes, arteriosclerosis, hypertension, hyperlipidemia, liver diseases, stroke, myocardial infarction, ischemic diseases, and cardiovascular diseases.

3. The method of claim 1, wherein the strain is administered in a composition in a content of $10^7$-$10^{12}$ cfu/g relative to a total weight of the composition.

* * * * *